United States Patent
Kruschel et al.

(10) Patent No.: US 8,768,037 B2
(45) Date of Patent: Jul. 1, 2014

(54) METHOD FOR CORRECTING IMAGE ARTIFACTS OCCURING AS A RESULT OF AN ANTI SCATTER GRID

(71) Applicants: Christian Kruschel, Hanstedt (DE); Christoph Köhler, Forchheim (DE)

(72) Inventors: Christian Kruschel, Hanstedt (DE); Christoph Köhler, Forchheim (DE)

(73) Assignee: Siemens Aktiengesellschaft, München (DE)

( * ) Notice: Subject to any disclaimer, the term of this patent is extended or adjusted under 35 U.S.C. 154(b) by 16 days.

(21) Appl. No.: 13/710,727

(22) Filed: Dec. 11, 2012

(65) Prior Publication Data

US 2013/0148786 A1   Jun. 13, 2013

(30) Foreign Application Priority Data

Dec. 12, 2011   (DE) .......................... 10 2011 088 265

(51) Int. Cl.
*G06K 9/00* (2006.01)
(52) U.S. Cl.
USPC ......................................... 382/132; 382/275
(58) Field of Classification Search
USPC .......... 382/130, 131, 132, 240, 248, 264, 275
See application file for complete search history.

(56) References Cited

U.S. PATENT DOCUMENTS

| | | | |
|---|---|---|---|
| 6,285,781 B1 | 9/2001 | Yamazaki | |
| 8,363,919 B2 * | 1/2013 | Sebok | 382/131 |
| 8,559,754 B2 * | 10/2013 | Fujita | 382/275 |
| 2012/0177267 A1 * | 7/2012 | Chen et al. | 382/131 |

FOREIGN PATENT DOCUMENTS

EP   1081947 A2   3/2001

* cited by examiner

*Primary Examiner* — Phuoc Tran

(57) ABSTRACT

A method for correcting image artifacts is proposed. The artifacts occur as a result of an anti scatter grid connected rigidly to an x-ray detector in recording three-dimensional image datasets. Two-dimensional projection images of an object are recorded from different recording geometries for reconstruction the three-dimensional image dataset. A calibration image is recorded for each recording geometry. An average image from all recorded calibration images is established. Subtraction images are established by subtracting the average image from the corresponding calibration images. Noise is removed from the subtraction images. The subtraction images and the average image are stored. A correction image is established for each recording geometry by addition of the subtraction image assigned to the recording geometry and of the average image and is used for correcting the projection image.

8 Claims, 2 Drawing Sheets

METHOD FOR CORRECTING IMAGE ARTIFACTS OCCURING AS A RESULT OF AN ANTI SCATTER GRID

CROSS REFERENCE TO RELATED APPLICATIONS

This application claims priority of German application No. 10 2011 088 265.0 filed Dec. 12, 2011, which is incorporated by reference herein in its entirety.

FIELD OF INVENTION

The application relates to a method for correction of image artifacts occurring because of an anti scatter grid connected rigidly to the x-ray detector during the recording of three-dimensional image datasets with an x-ray device with a C-arm, on which an x-ray source and the x-ray detector are arranged opposite one another, wherein two-dimensional projection images of an object are recorded from different recording geometries and used for a reconstruction of the three-dimensional image dataset. The application also relates to an x-ray device.

BACKGROUND OF INVENTION

C-arm x-ray devices, i.e. x-ray devices having a C-arm and on which an x-ray source and an x-ray detector are provided opposite one another are already known in the prior art. As a result of at least one degree of freedom of movement of the C-arm, at least one rotation facility, the x-ray detector and the x-ray source can be moved around an object to be imaged, such as a patient, so that images can be recorded from different projection angles, i.e. from different projection geometries.

To avoid influences from scattered rays, these types of x-ray device mostly have what is referred to as an anti scatter grid, which ultimately consists of a grid placed on the x-ray detector. Focused anti scatter grids are used in such cases, which are permanently connected to the x-ray detector and are set to a usual distance between the x-ray source and the x-ray detector, as are needed for explicit, such as high-resolution, two-dimensional diagnostic x-ray images, known as radiography images.

In the interim however it has also been proposed that three-dimensional images be recorded by an x-ray device with a C-arm, by a method similar to that of computed tomography (CT) being used, giving rise to the frequently used name C-arm CT. In such cases two-dimensional projection images are mostly recorded along a recording trajectory, mostly by rotation of the C-arm, from different recording geometries including different projection directions, from which three-dimensional image datasets can then be constructed using usual methods, for example by iterative reconstruction or filtered back projection (FBP). The three-dimensional image dataset in such cases ultimately contains a three-dimensional volume of the attenuation coefficients which describes the target.

The said anti scatter grid not only leads to a reduction in scattered radiation but also in the desired primary radiation since it has a structure, such as a grid structure, also partly blocking the primary radiation. This leads to artifacts in the x-ray projection image, which in their turn lead to a reduced image quality in the reconstructed image dataset. In order to reduce these artifacts it is known that pixel-based gain correction can be undertaken by a correction image, which for example can be obtained by calibration. In such cases not just the effect of the grid structures of the anti scatter grid can be taken into account by such a correction image, but also a problem which frequently arises precisely with C-arm CT, since a greater distance between the x-ray source and the x-ray detector is used than that for which the anti scatter grid is focused, so that in the final analysis the images are recorded with a defocused anti scatter grid, which leads to an unequal intensity distribution, to a reduction in intensity at the edges of the detector, even with homogeneous illumination.

In conjunction with such an intensity reduction, as a result of a defocused anti scatter grid, a further disadvantageous effect is also to be observed in C-arm CT, namely the fact that, because of mechanical inaccuracies of the x-ray device, deviations occur at different recording times, i.e. with different recording geometries, in respect of the position of the focus of the x-ray source relative to the x-ray detector. This also results in displacement of the artifact patterns and also to the said intensity distribution, which can lead to clearly visible edges in the reconstructed volume, although this effect is barely perceptible in the projection images. These types of mechanical inaccuracies of the x-ray device are based on the fact that the C-arm is not rigid and thus for example, in different positions of the C-arm, a different gravity influences the x-ray device in different ways.

The said mechanical inaccuracies ultimately do not allow a global correction, including a single correction image, to be used for all recording geometries, since this in turn can lead to the retention of artifacts or to the occurrence of new artifacts, as described.

To resolve this problem it has been proposed that a separate pixel-based correction image be created and kept for each recording geometry, including each projection image to be recorded. The correction image is determined by a calibration measurement, wherein for example, to arrive at similar intensity values as during the imaging of a patient, a copper plate can be introduced into the radiation path. Since noise is a critical parameter in the reconstruction, since for example the noise is directly correlated to patients with the patient dose, the correction image may only contain a very small noise amount. In the prior art, to obtain good correction images, a plurality of calibration images is recorded and averaged for each recording geometry, which demands a high calibration effort. Removing noise from the images by simple smoothing, for example a Gaussian filter, does not resolve the problem since the pattern of the artifacts on the correction images is also destroyed by this, so that the correction can no longer rectify the destroyed artifact pattern. A further disadvantage of the known method is that a very high amount of memory space is required to store correction images for each imaging geometry, since the significant structures would also be lost within the framework of a compression.

SUMMARY OF INVENTION

The underlying object of the application is thus to specify a method for correction of recorded images in respect of artifacts caused by an anti scatter grid which takes sufficient account of the mechanical imprecisions, makes do with a reduced calibration effort and also reduces the memory space requirement for the correction images.

To achieve this object in accordance with the application, in a method of the type described at the start, the following steps are provided:
Recording of a respective calibration image for each recording geometry,
Establishing an average image from all recorded calibration images, Establishing subtraction images for all imaging geometries by subtracting the average image from the corresponding calibration images, Smoothing the subtraction images to remove noise from the subtraction images, and Storing the subtraction images and the average image, wherein, to correct recorded projection images for each recording geometry a correction image is established by addition of the subtraction image assigned to the recording geometry and the average image and the correction image is used for correction of the projection image.

The application addresses the problem of establishing a smoothed, i.e. noise-reduced, correction image for each recording geometry which also still contains the artifact pattern which was triggered by the anti scatter grid. To this end a single calibration image is first recorded for each recording geometry. The single calibration images, as has already been mentioned, are affected by noise, so that they cannot be used directly as correction images.

It is thus now proposed in accordance with the application that an average image of all recorded calibration images first be calculated. Since the anti scatter grid is permanently connected to the x-ray detector, the corresponding artifact patterns initiated directly by the anti scatter grid with high frequencies in the local space are always the same, so that the average image of this information contains high local frequencies of the anti scatter grid, while noise is reduced on account of the statistical consideration of a plurality of calibration images. The said mechanical imprecisions of the x-ray device contribute to this high-frequency information because of the relative movement which is not present between anti scatter grid and x-ray detector.

The average image is then subtracted from each recorded calibration image in order to obtain subtraction images. These subtraction images thus also no longer contain the artifact pattern with high local frequencies and can be smoothed. Patterns remaining to be corrected, for example an intensity distribution as a result of an anti scatter grid not focused for the distance between x-ray detector and x-ray source during the recording of the calibration images, change to somewhat larger distances, thus exhibit low local frequencies which are retained even with smoothing, which can be local in accordance with the application. In this way it is thus possible to "denoise" the subtraction images and then store them, compressed together with the average image.

In order to obtain the actual correction image to be used for a given recording geometry the average image must now merely—if necessary after a decompression of the stored subtraction image—be added to the subtraction image. Lastly the high-frequency information of the artifact pattern independent of the actual imaging geometry is preserved by the establishment of the average image and its subtraction on the one hand on the basis of the average image, on the other hand removed from further consideration with respect to removal of noise since it has been recognized that the artifact information dependent on the recording geometry lies at the low local frequencies. Thus noise removal by smoothing is possible precisely when the high-frequency artifact patterns can no longer be lost.

As has been shown, the disclosed method relates in its actual problem-solving mainly to cases in which, during recording of the projection images, a defocused anti scatter grid is present and simultaneously mechanical imprecisions, triggered because of the non-perfect rigidity of the C-arm, in relation to gravitational force. The disclosed method can thus be applied if the anti scatter grid is focused for a different distance between the x-ray detector and the x-ray source than the distance used for recording the projection images and/or, under the influence of gravity, a displacement of the x-ray source from the x-ray detector and thus the anti scatter grid occurs at different positions of the C-arm.

Overall the disclosed method makes it possible, with a greatly reduced calibration effort, to significantly reduce the level of artifacts in reconstructed image datasets, since the noise can be greatly reduced despite only a single calibration image being recorded.

While it is basically conceivable to take account of smoothing using a Gaussian filter, this is not local however and may thus result in the loss of artifact patterns of mid or also low local frequencies.

There can thus be provision within the framework of the present application in an manner for a local smoothing algorithm based on variation to be used for smoothing the subtraction images, wherein a minimization of the sum of a standard and a regularization functional accompanying a weighting factor is undertaken. In this way the method works locally so that artifact patterns of mid and low-frequencies which are triggered by the changed recording conditions in the respective recording geometry are also retained in an improved manner. Such a local smoothing algorithm based on variation can also be written mathematically as a minimization problem, in formulas as $$\min_{U_i^* \in M} \left[ \int (U_i(x) - U_i^*(x))^2 dx + \lambda \psi(x) \right].$$

In this equation $U_i^*$ designates the desired smoothed subtraction image, $U_i$ designates the initial subtraction image and the function $\Psi$ designates a regularization functional, which must be suitably selected $\lambda$ is a weighting factor which makes possible fine adjustment and M is the minimization space, i.e. the space from which the solutions are selected.

While it is now basically possible to undertake a usual TV (total variation) smoothing, a Sobolev regularization is used, in which the Sobolev space $W^{1,p}$ is considered as the solution space for the minimization. The standard mentioned is selected in this case as the standard assigned to the Sobolev space. p is selected as greater than 1, but as close to 1 as possible, for example as p=1.1, since it has been shown here that in this way a smoothing of the subtraction images with sufficient preservation of the information about the artifact pattern is possible in an outstanding manner. Another good choice relates to the space $W^{1,1}$ with Radon dimensions.

As already mentioned, a further problem that exists with current methods, those that keep correction images averaged from a number of calibration images for each recording geometry, is the high storage space requirement. It is thus desirable to be able to compress the correction images (at least partly) while the artifact patterns can be retained. Since in accordance with the application there is a division in the higher-frequency artifact patterns into the average image and the subtraction images, there can be provision for the subtraction images to be compressed before being stored with a compression algorithm. In such cases in must be ensured that any loss of information occurring does not relate to the artifact patterns of mid or high local frequencies remaining in the subtraction images, so that there can be provision for a wavelet compression algorithm, such as using a CDF9/7 or a CDF5/3 wavelet. In such cases a wavelet compression method can be included with soft thresholding and variable threshold value. Soft thresholding ultimately means that when the threshold is reached there is not a jump in the compression function, but the linear curve beginning at 0 begins directly after the threshold value since good results can be achieved hereby. A variable threshold value is to be understood as the threshold value itself being selected for detail spaces as a function of the local frequencies, thus being variable itself. This concept is also summarized as "Bayesian soft thresholding". Suitable wavelets have already been described, wherein the CDF5/3 wavelet allows lossless compression, with the CDF9/7 wavelet a lossy compression is possible.

With a suitable choice of the compression method the present application for example allows a reduction in the storage space required to around 7%. Thus in any event there is a marked saving.

As well as the method, the present application also relates to an x-ray device with a C-arm, on which an x-ray source and an x-ray detector are disposed opposite one another, having an anti scatter grid connected rigidly to the x-ray detector and a control device embodied for carrying out the disclosed method. All information given in relation to the disclosed method can be transferred similarly to the disclosed x-ray device, with which the present application can thus likewise be obtained. The control device automatically carries out the disclosed method, for which for example suitable hardware and/or software components can be provided.

BRIEF DESCRIPTION OF THE DRAWINGS

Further features and details of the present application emerge from the embodiments described below, as well as with reference to the drawings, in which.

DETAILED DESCRIPTION OF INVENTION

The disclosed method, thus also the embodiment shown, involves a correction of artifacts occurring as a result of an anti scatter grid connected rigidly to the x-ray detector, thus in concrete terms to a correction of the projection images which are used for a three-dimensional reconstruction such that artifacts in the three-dimensional dataset are reduced. Such artifacts, as are considered in the embodiment shown here, ultimately have different causes. In addition to the artifact patterns which are necessarily produced by shadowing by a grid of the anti-scatter grid, intensity variations can also occur if an anti-scatter grid not focused on the correct distance between the x-ray source and the x-ray detector is used or the distance between the x-ray detector and the x-ray source is not adjusted so that the focusing distance is produced. These image effects related to shadowing are independent of the actual recording geometry, wherein effects also occur in any event which are dependent on the recording geometry, for example on mechanical imprecisions of the x-ray device, such as effects triggered by the C-arm. These are usually based on a relative displacement of the focus of the x-ray source and the x-ray detector with the anti scatter grid, for example as a result of effects of gravity. The displacement of the focus relative to the detector also causes a displacement of the aforementioned non-homogeneous intensity distribution, so that edge artifacts and the like can occur during its correction.

The embodiment of the disclosed method shown here relates in concrete terms of creating, with little measurement effort, suitable correction images for the different recording geometries, which still always contain all relevant artifact patterns and are able to be stored efficiently.

Figure 1:
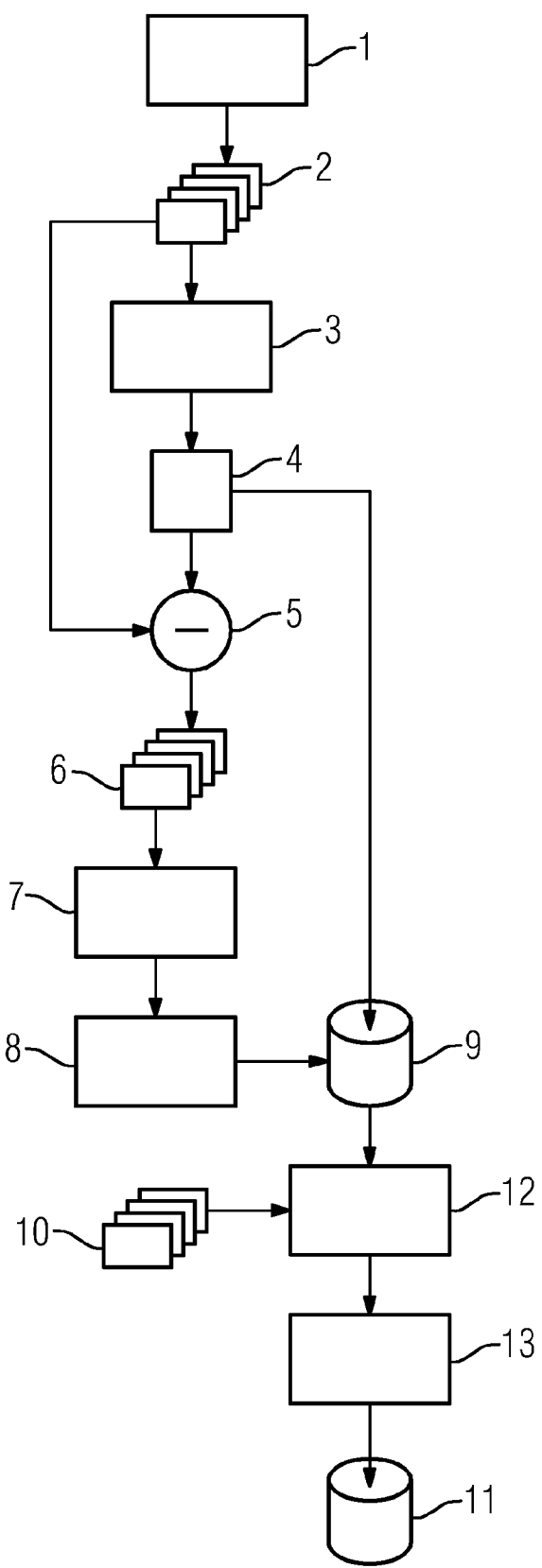
FIG. 1 shows a flow diagram of the disclosed method.

To this end in a step 1, cf. FIG. 1, calibration images 2 are first recorded, wherein for each recording geometry considered here only a single calibration image 2 is necessary. For example in such cases homogeneous illumination can be ensured by a copper plate.

In a step 3 all these two-dimensional calibration images 2 are now averaged, so that a single average image 4 is obtained. The average image 4 contains the information linked to high frequencies in the local space about the artifact patterns arising from the shadowing by the anti-scatter grid, since these always arise independently of the recording geometry, since the anti scatter grid is connected in a fixed position to the x-ray detector.

In a step 5 subtraction images 6 are now formed, by the average image 4 being subtracted from the calibration images 2 in each case.

The subtraction images 6 are now smoothed in a step 7, wherein a local smoothing method based on variation is used. In concrete terms, in the embodiment presented here, a Sobolev regularization is used in this case, wherein the Sobolev space $W^{1,p}$ is used here as the solution space, here for example with p=1.1, wherein the corresponding standard is also used of course. It is thus possible to remove noise from the subtraction images 6, wherein at the same time artifact patterns or effects resulting from the anti-scatter grid, for example a displaced intensity distribution, which lie at mid and/or low local frequencies, are retained. Thus denoised, i.e. less noisy, subtraction images 6 are obtained as the result of step 7.

These denoised subtraction images 6 are now compressed in a step 8, wherein a wavelet compression with soft thresholding and variable threshold value is used. In this case the CDF9/7 wavelet is used here.

The smoothed, compressed subtraction images 6 and the average image 4 are kept as a correction dataset 9 in a memory device for later use in the correction of projection images. The memory device in this case can be part of a control device of the x-ray device carrying out the method.

For correction of projection images 10 recorded with different recording geometries, from which a three-dimensional image dataset 11 is to be reconstructed, correction images are now initially established in a step 12 by the smoothed, compressed subtraction images 6 being decompressed and then the average image and the respective smoothed, decompressed subtraction images 6 being summed for the recording geometry which is needed Likewise in step 12 the projection images 10 are corrected by using the correction images thus obtained.

Then, using the corrected projection images 10, in a step 13 the reconstruction of the three-dimensional image datasets 11 is undertaken, wherein for example a method of filtered back projection or of iterative reconstruction can be used.

Figure 2:
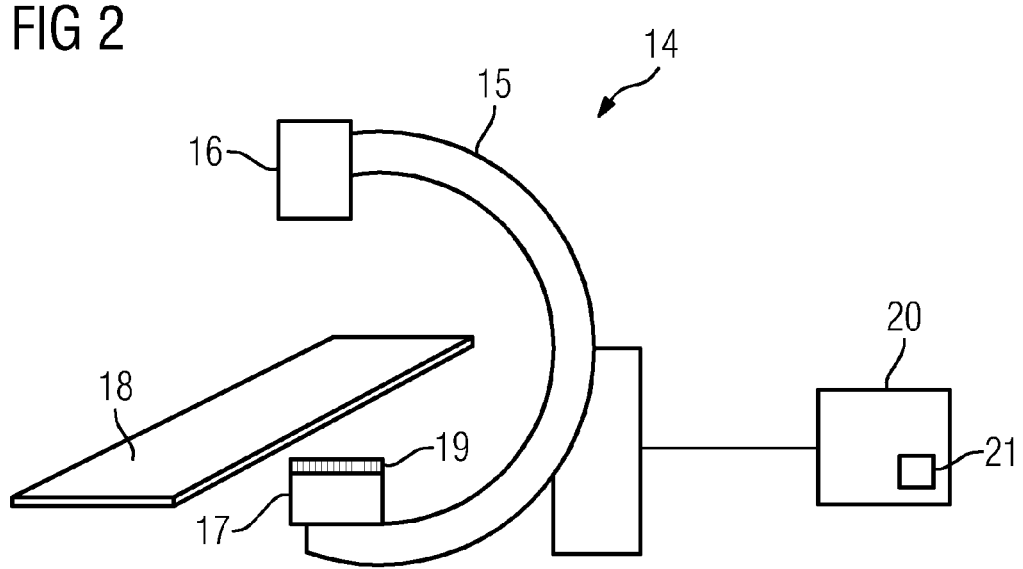
FIG. 2 shows a basic diagram of a disclosed x-ray device

FIG. 2 shows a basic diagram of a disclosed x-ray device 14. This comprises a C-arm 15 on which an x-ray source 16 and an x-ray detector 17 are disposed opposite one another. The C-arm 15 can in this case be pivoted around a least one axis around a patient couch 18 on which a patient not shown in any greater detail here can be disposed, in order to be able to record x-ray images or projection images of different recording geometries, thus from different projection directions. To effectively reduce scattered radiation an anti-scatter grid 19 is mounted on the x-ray detector 17, in a fixed position relative to the latter.

The anti scatter grid 19 is focused at a specific distance between the x-ray detector 17 and the x-ray source 16, wherein this distance is selected as ideal for enabling two-dimensional radiography x-ray images, i.e. two-dimensional diagnostic fluoroscopy images to be recorded. If projection images 10, from which a three-dimensional image dataset 11 is to be reconstructed are to be recorded, the maximum possible distance between the x-ray detector 17 and the x-ray source 16 is however mostly selected, so that the anti scatter grid 19 is not focused for this distance.

There is also the additional factor that mechanical imprecisions occur when the C-arm 15 is used, for example as a result of it not being embodied entirely rigidly and the different effects of gravity on the x-ray source 16 and the x-ray detector 17 with the anti scatter grid 19. This leads to a slight displacement of the focus of the x-ray source 16 in relation to the x-ray detector 17 and the anti scatter grid 19, which is also perceptible in the projection images as an effect of the anti scatter grid 19.

The x-ray device 14 further comprises a control device 20 for its control, which is embodied for carrying out the method according to the application. To this end the control device 20 has a storage device 21 for storing the correction dataset 9 with the smoothed, compressed subtraction images 6 and the average image 4.

Although the application has been illustrated and described in greater detail by the embodiment, the application is not restricted by the disclosed examples and other variations can be readily derived by the person skilled in the art, without departing from the scope of protection of the application.

The invention claimed is:

1. A method for correcting image artifacts resulting from an anti scatter grid rigidly connected to an x-ray detector disposed on a C-arm of an x-ray device, comprising:
   recording a plurality of two-dimensional projection images of an object from different recording geometries using the x-ray device;
   recording a plurality of calibration images for each of the recording geometries respectively using the x-ray device;
   determining an average image from the calibration images using a control device;
   determining subtraction images for the each of the recording geometries by subtracting the average image from the corresponding calibration images respectively;
   smoothing the subtraction images by removing noise from the subtraction images;
   storing the smoothed subtraction images and the average image in the control device;
   determining correction images for the each of the recording geometries by adding the smoothed subtraction images assigned to the each of the recording geometries respectively with the average image; and
   correcting the recorded projection images based on the correction images.

2. The method as claimed in claim 1, wherein an x-ray source is disposed on the C-arm opposite to the x-ray detector, wherein the anti scatter grid is focused at a different distance between the x-ray source and the x-ray detector than a distance for recording the projection images, and wherein a displacement of the x-ray source in relation to the x-ray detector and a displacement of the anti scatter grid occur at different positions of the C-arm under an influence of gravity.

3. The method as claimed in claim 1, wherein the subtraction images are smoothed using a local smoothing algorithm based on a variation, wherein sum of a standard and of a functional regularization with a weighting factor is minimized in smoothing the subtraction images.

4. The method as claimed in claim 3, wherein the regularization comprises a Sobolev regularization in which a Sobolev space $W^{1,p}$ is a solution space for the minimization.

5. The method as claimed in claim 1, wherein the smoothed subtraction images are compressed with a compression algorithm before storing in the storage device.

6. The method as claimed in claim 5, wherein the compression algorithm comprises a wavelet compression algorithm.

7. The method as claimed in claim 6, wherein the wavelet compression algorithm comprises a CDF9/7 or a CDF5/3 wavelet.

8. An x-ray device, comprising:
   a C-arm on which an x-ray source and the x-ray detector are disposed opposite one another;
   an anti scatter grid connected rigidly to the x-ray detector; and
   a control device adapted to perform the method as claimed in claim 1.

* * * * *